United States Patent
Cottrell

(10) Patent No.: US 6,225,515 B1
(45) Date of Patent: *May 1, 2001

(54) PROCESS FOR THE PURIFICATION OF A DIOLEFIN HYDROCARBON STREAM

(75) Inventor: Paul R. Cottrell, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/359,629

(22) Filed: Jul. 22, 1999

(51) Int. Cl.$^7$ ...................................... C07C 5/08
(52) U.S. Cl. ................ 585/259; 585/258; 585/810; 208/296
(58) Field of Search ................... 585/258, 259, 585/810; 208/296

(56) References Cited

U.S. PATENT DOCUMENTS

| | | | |
|---|---|---|---|
| 3,407,227 | * 10/1968 | Beck et al. ........................ | 554/144 |
| 3,496,069 | * 2/1970 | Tschopp et al. .................... | 203/53 |
| 3,634,536 | 1/1972 | Frevel et al. ................. | 260/681.5 R |
| 3,637,888 | * 1/1972 | Cahn et al. ...................... | 585/259 |
| 3,655,806 | * 4/1972 | Brandt et al. ..................... | 585/803 |
| 3,692,852 | * 9/1972 | Tabler ............................. | 585/274 |
| 3,751,508 | * 8/1973 | Fugiso et al. ..................... | 585/262 |
| 3,912,789 | * 10/1975 | Frevel et al. ..................... | 585/259 |
| 4,049,742 | * 9/1977 | Weitz et al. ...................... | 585/258 |
| 4,277,313 | * 7/1981 | Mehra et al. ...................... | 203/32 |
| 4,440,956 | 4/1984 | Couvillion ........................ | 585/260 |
| 4,831,200 | * 5/1989 | Debras et al. ..................... | 585/259 |
| 6,040,489 | * 3/2000 | Imai .............................. | 585/260 |

* cited by examiner

Primary Examiner—Walter D. Griffin
Assistant Examiner—Nadine Preisch
(74) Attorney, Agent, or Firm—John G. Tolomei; John G. Cutts, Jr.

(57) ABSTRACT

A process for the selective hydrogenation of trace quantities of acetylene compounds contained in a stream of diolefins to achieve extended on-stream performance by contacting an off-line selective hydrogenation reaction zone containing selective catalyst with hydrogen and a polymer solvent.

8 Claims, 1 Drawing Sheet

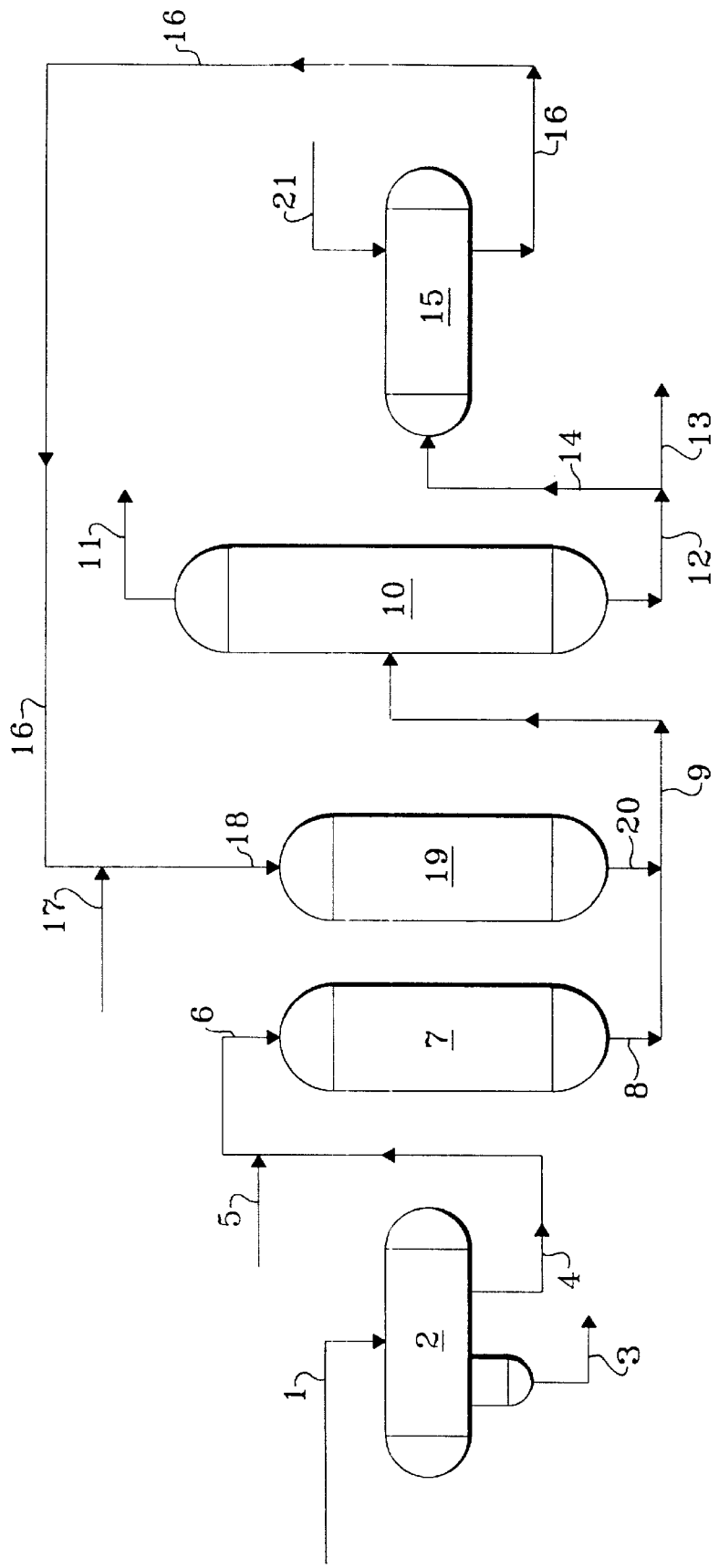

PROCESS FOR THE PURIFICATION OF A DIOLEFIN HYDROCARBON STREAM

BACKGROUND OF THE INVENTION

The field of art to which this invention pertains is the purification of a diolefin hydrocarbon stream containing trace quantities of acetylene compounds. The production of diolefins is well known and widely practiced to produce a wide variety of products and precursor products utilizing a variety of diolefin production processes including naphtha cracking processes and by-products from fluid catalytic cracking processes. Most of these diolefin production processes produce undesirable trace quantities of acetylene. One technique which is used purify diolefin streams selectively hydrogenates the acetylene while minimizing the destruction or hydrogenation of the diolefin compounds.

The selective hydrogenation of the acetylene compounds is generally conducted in the presence of a selective hydrogenation catalyst and hydrogen and conducted at an elevated pressure and temperature. Such selective hydrogenation catalysts are well known in the art and include, for example, a catalyst containing copper metal associated with one or more activator metals impregnated on an alumina support. During the acetylene hydrogenation polymers are formed and deposited on the catalyst thereby reducing the activity of the catalyst. One known method of regenerating spent or partially spent catalyst is to perform a controlled carbon burn and subsequent metal reduction to remove catalyst contaminants which are formed as an undesirable by-product of the acetylene hydrogenation. The carbon burn regeneration techniques necessarily require that the reaction zone containing the spent catalyst be taken off-line and that ancillary regeneration equipment be provided.

INFORMATION DISCLOSURE

U.S. Pat. No. 3,634,536 (Frevel et al) discloses a process for selectively hydrogenating acetylenic impurities in an isopropene- or butadiene-containing stream whereby carbon monoxide is utilized during hydrogenation over a copper-based catalyst.

U.S. Pat. No. 4,440,956 (Couvillion) discloses a catalyst for the removal of acetylenes from liquid hydrocarbon streams with a minimum loss of diolefinic unsaturation present in the liquid composition.

Although a wide variety of process flow schemes, operating conditions and catalysts have been used in commercial activities, there is always a demand for new selective hydrotreating processes which provide lower costs, higher selectivity and longer on-stream operation.

The present invention is able to maintain the high activity of the selective hydrogenation catalyst by discontinuing the flow of diolefinic hydrocarbon feedstock to at least one off-line hydrogenation reaction zone and contacting the at least partially spent catalyst with hydrogen and a polymer solvent in order to recover at least a portion of the lost activity.

BRIEF SUMMARY OF THE INVENTION

The present invention is a selective acetylene hydrogenation process which is able to produce a high quality diolefin hydrocarbon having extremely low levels of acetylene over an extended period because of the ability to readily regenerate catalyst contained in an off-line reaction zone while continuing to operate an on-line selective hydrogenation reaction zone. The spent or partially spent catalyst is contacted with hydrogen and a polymer solvent in order to restore at least a portion of the fresh catalyst activity.

In accordance with one embodiment, the present invention relates to a process for the purification of a diolefin hydrocarbon stream containing trace quantities of acetylene compounds and the cyclic regeneration of an at least partially spent selective hydrogenation catalyst which process comprises: (a) introducing the diolefin hydrocarbon stream containing trace quantities of acetylene compounds and elemental hydrogen into a selective hydrogenation zone to selectively hydrogenate at least a portion of the acetylene compounds and to produce an at least partially spent selective hydrogenation catalyst; (b) passing the resulting effluent from the selective hydrogenation zone in step (a) to a fractionation zone to produce a diolefin hydrocarbon stream having a reduced concentration of acetylene compounds; (c) contacting the at least partially spent selective hydrogenation catalyst in the selective hydrogenation zone with a polymer solvent and hydrogen to reduce the polymer content of the selective hydrogenation catalyst to thereby increase hydrogenation activity; (d) passing the resulting effluent from the selective hydrogenation zone to the fractionation zone to produce a stream comprising polymer solvents and polymer compounds; (e) recycling at least a portion of the stream comprising polymer solvent and polymer compounds to provide at least a portion of the polymer solvent in step (c); (f) recovering at least another portion of the stream comprising polymer solvent and polymer compounds; (g) recovering the diolefinic hydrocarbon stream having a reduced concentration of acetylene compounds produced in step (b); and (h) introducing the diolefin hydrocarbon stream containing trace quantities of acetylene compounds and elemental hydrogen into the selective hydrogenation zone after contact with the polymer solvent and hydrogen.

In accordance with another embodiment, the present invention relates to a process for the purification of a butadiene hydrocarbon stream containing trace quantities of acetylene compounds and the cyclic regeneration of an at least partially spent selective hydrogenation catalyst which process comprises: (a) introducing the butadiene hydrocarbon stream containing trace quantities of acetylene compounds and elemental hydrogen into a selective hydrogenation zone to selectively hydrogenate at least a portion of the acetylene compounds and to produce an at least partially spent selective hydrogenation catalyst; (b) passing the resulting effluent from the first selective hydrogenation zone in step (a) to a fractionation zone to produce a butadiene hydrocarbon stream having a reduced concentration of acetylene compounds; (c) contacting the at least partially spent selective hydrogenation catalyst in the selective hydrogenation zone with a hexane solvent and hydrogen to reduce the polymer content of the selective hydrogenation catalyst to thereby increase hydrogenation activity; (d) passing the resulting effluent from the selective hydrogenation zone to the fractionation zone to produce a stream comprising hexane solvent and polymer compounds; (e) recycling at least a portion of the stream comprising hexane solvent and polymer compounds to provide at least a portion of the hexane solvent in step (c); (f) recovering at least another portion of the stream comprising hexane solvent and polymer compounds; (g) recovering the butadiene hydrocarbon stream having a reduced concentration of acetylene compounds produced in step (b); and (h) introducing the butadiene hydrocarbon stream containing trace quantities of acetylene compounds and elemental hydrogen into the selective hydrogenation zone after contact with the hexane solvent and hydrogen.

BRIEF DESCRIPTION OF THE DRAWING

The drawing is a simplified process flow diagram of a preferred embodiment of the present invention. The drawing is intended to be schematically illustrative of the present invention and not be a limitation thereof.

DETAILED DESCRIPTION OF THE INVENTION

It has been discovered that a selective hydrogenation process for the hydrogenation of trace quantities of acetylene contained in a stream of diolefins may achieve long-term high activity, good yields and product quality by contacting an off-line reaction zone containing the selective catalyst with a polymer solvent and hydrogen. Simultaneously, at least one other reaction zone containing the selective hydrogenation catalyst remains on-line in order to maintain the continuous production of a hydrogenated diolefin stream having a reduced concentration of acetylene compounds. These advantages enable superior performance and economic results.

The process of the present invention is particularly useful for the production of high quality diolefin streams in a process having an extended on-stream capability. The diolefin feed stream may be any convenient hydrocarbon stream containing diolefin compounds and having undesirable trace quantities of acetylene compounds. It is contemplated that the diolefin feedstream contains diolefins containing from 3 to about 5 carbon atoms. A preferred diolefin feedstream contains butadiene.

In accordance with the present invention, the selected diolefin feedstock is introduced along with hydrogen into an on-line selective hydrogenation reaction zone operating at selective hydrogenation conditions and containing a selective hydrogenation catalyst to produce an improved diolefin stream having a reduced concentration of acetylene compounds. The selective hydrogenation conditions will depend upon the selected diolefinic feed and may preferably be selected from a pressure from about 200 psig to about 500 psig and a temperature from about 90° F. to about 180° F.

In an alternating fashion, an off-line reaction zone containing selective hydrogenation catalyst, either spent or partially spent, is preferably contacted with a polymer solvent and hydrogen at catalyst regeneration conditions including a pressure from about 150 psig to about 500 psig, a temperature from about 90° F. to about 500° F. and a solvent liquid hourly space velocity from about 0.5 to about 10 hr$^{-1}$. The polymer solvent may be selected from any compound or mixtures of compounds and which polymer solvent is capable of acting as a solvent for polymers which are produced during the selective hydrogenation reaction. Suitable solvents may be selected from alkane compounds having from about 4 to about 8 or more carbon atoms. In the case where the fresh feedstock is a stream of butadiene, a particularly preferred polymer solvent is hexane. It is preferred that the polymer solvent has a boiling point greater than the diolefin feedstream. The resulting effluent containing polymer solvent, dissolved polymer and hydrogen from the off-line reaction zone undergoing regeneration is introduced into a fractionation zone to remove gaseous hydrogen and to recover the polymer solvent which is preferably recycled together with fresh, make-up polymer solvent. A small drag stream containing polymer solvent and polymer is removed from the process in order to prevent an undesirable buildup of polymer. The fresh make-up of polymer solvent is added in order to maintain a suitable inventory of solvent. At least a portion of the polymer solvent recovered from the fractionation zone is preferably recycled to the inlet of the off-line selective hydrogenation zone.

The resulting effluent from the on-line selective hydrogenation reaction zone is passed to a fractionation zone to produce a diolefin hydrocarbon stream having a reduced concentration of acetylene compounds and a stream containing polymer compounds which are recovered and removed from the process.

The selective hydrogenation catalyst may be any suitable known catalyst and may contain one or more beds of the same or different selective hydrogenation catalyst. Suitable catalysts for the selective hydrogenation of acetylene contain copper metal, activated with one or more of the metals from the group of silver, platinum, palladium, manganese, cobalt, nickel, chromium and molybdenum on an alumina support. The hydrogenation catalysts contemplated for use in the process of the present include any support types, sizes and shapes, for example, spheres, cylinders, tri-lobes, quadralobes and rings. The process of the present invention is not limited by the type of hydrogenation catalyst and any suitable selective hydrogenation catalyst is contemplated for use therein.

DETAILED DESCRIPTION OF THE DRAWING

In the drawing, the process of the present invention is illustrated by means of a simplified schematic flow diagram in which such details as instrumentation, heat-exchange, and heat-recovery circuits, separation facilities and similar hardware have been deleted as being non-essential to an understanding of the techniques involved.

With reference now to the drawing, a feedstream comprising butadiene, trace quantities of acetylene and steam condensate is introduced into the process via line 1 and is passed into feed surge drum 2. A condensed steam stream is removed from feed surge drum 2 via line 3 and recovered. A stream containing butadiene and trace quantities of acetylene is removed from feed surge drum 2 via line 4 and is admixed with a hydrogen-rich gaseous stream provided via line 5 and the resulting admixture is introduced into on-line selective hydrogenation zone 7 via line 6. An effluent stream containing butadiene and having a reduced concentration of acetylene compounds is removed from on-line selective hydrogenation zone 7 via lines 8 and 9 and introduced into fractionation zone 10. A stream containing butadiene and having a reduced concentration of acetylene compounds is removed from fractionation zone 10 via line 11 and is recovered for further purification and subsequent use. A stream containing polymer solvent and polymer compounds is removed from surge drum 15 via line 16 and is admixed with a hydrogen-rich gaseous stream introduced via line 17 and the resulting admixture is transported via line 18 and introduced into off-line selective hydrogenation zone 19. An effluent stream containing polymer solvent and polymer compounds is removed from off-line selective hydrogenation zone 19 via line 20 and line 9 and is introduced into fractionation zone 10. A stream containing polymer solvent and polymer compounds is removed from fractionation zone 10 via line 12 and at least a portion is transported via line 14 and introduced into polymer solvent storage drum 15. Another portion of the stream removed from fractionation zone 10 via line 12 is removed via line 13 as a drag stream in order to prevent an undue accumulation of polymer compounds in the process. Fresh make-up polymer solvent is introduced via line 21 into polymer solvent storage drum 15.

The process of the present invention is further demonstrated by the following illustrative embodiment. This illustrative embodiment is, however, not presented to unduly limit the process of this invention, but to further illustrate the advantages of the hereinabove-described embodiment. The following results were not obtained by the actual performance of the present invention but are considered prospective and reasonably illustrative of the expected performance of the invention based upon sound engineering calculations.

ILLUSTRATIVE EMBODIMENT

A raw butadiene stream in an amount of 100 mass units and having the characteristics presented in Table 1 is introduced into a fresh feed drum and entrained or condensed water is decanted therefrom. The raw butadiene stream is then admixed with 1 mass units of hydrogen and the resulting admixture is introduced into a fixed bed of selective hydrogenation catalyst contained in an on-line selective hydrogenation zone. The catalyst contains copper metal. The resulting effluent from the on-line selective hydrogenation zone is introduced into a fractionation zone to produce a butadiene stream containing less than 3 wppm acetylene compounds (a 99.9% reduction).

An off-line selective hydrogenation zone containing a selective hydrogenation catalyst having a copper metal component is contacted with a stream containing hexane and hydrogen at regeneration conditions including a pressure of 280 psig, a temperature of 300° F. and a liquid hourly space velocity (LHSV) of 1.3 $hr^{-1}$. The resulting effluent containing hexane, hydrogen and polymer compounds from the off-line selective hydrogenation zone is also introduced into the previously mentioned fractionation zone to produce a stream containing hexane and dissolved polymer compounds. At least a portion of the recovered hexane in an amount of 0.35 mass units is removed from the process as a drag stream to prevent undue polymer compound accumulation and recovered. At least another portion of the recovered hexane is recycled along with fresh make-up hexane in an amount of 0.3 mass units to the off-line selective hydrogenation zone in order to continue the regeneration thereof.

TABLE 1

| RAW BUTADIENE STREAM ANALYSIS | |
|---|---|
| Butadiene | 50 weight % |
| Acetylene | 0.8 weight % |

The foregoing description, drawing and illustrative embodiment clearly illustrate the advantages encompassed by the process of the present invention and the benefits to be afforded with the use thereof.

What is claimed:

1. A process for the purification of a diolefin hydrocarbon stream containing trace quantities of acetylene compounds and the cyclic regeneration of an at least partially spent selective hydrogenation catalyst which process comprises:

(a) introducing said diolefin hydrocarbon stream containing trace quantities of acetylene compounds and elemental hydrogen into a selective hydrogenation zone to selectively hydrogenate at least a portion of said acetylene compounds and to produce an at least partially spent selective hydrogenation catalyst;

(b) passing the resulting effluent from said selective hydrogenation zone in step (a) to a fractionation zone to produce a diolefin hydrocarbon stream having a reduced concentration of acetylene compounds;

(c) contacting the at least partially spent selective hydrogenation catalyst in said selective hydrogenation zone with a polymer solvent consisting essentially of an alkane compound having from about four to about eight carbon atoms and hydrogen to reduce the polymer content of the selective hydrogenation catalyst to thereby increase hydrogenation activity;

(d) passing the resulting effluent from said selective hydrogenation zone to said fractionation zone to produce a stream comprising polymer solvents and polymer compounds;

(e) recycling at least a portion of said stream comprising polymer solvent and polymer compounds to provide at least a portion of said polymer solvent in step (c);

(f) recovering at least another portion of said stream comprising polymer solvent and polymer compounds;

(g) recovering said diolefinic hydrocarbon stream having a reduced concentration of acetylene compounds produced in step (b); and (h) introducing said diolefin hydrocarbon stream containing trace quantities of acetylene compounds and elemental hydrogen into said selective hydrogenation zone after contact with said polymer solvent and hydrogen.

2. The process of claim 1 wherein said diolefin hydrocarbon stream comprises butadiene.

3. The process of claim 1 wherein said selective hydrogenation zones contain a catalyst comprising copper metal.

4. The process of claim 1 wherein said first selective hydrogenation zone is operated at conditions including a pressure from about 200 to about 500 psig and a temperature from about 90° F. to about 180° F.

5. The process of claim 1 wherein the contacting in step (c) is conducted at conditions including a pressure from about 150 to about 500 psig, a temperature from about 90° F. to about 500° F., a solvent liquid hourly space velocity from about 0.5 to about 10 $hr^{-1}$.

6. The process of claim 1 wherein said polymer solvent is hexane.

7. The process of claim 1 wherein said diolefin hydrocarbon stream comprises a compound selected from the group of diolefins containing from about 3 to about 5 carbon atoms.

8. A process for the purification of a butadiene hydrocarbon stream containing trace quantities of acetylene compounds and the cyclic regeneration of an at least partially spent selective hydrogenation catalyst which process comprises:

(a) introducing said butadiene hydrocarbon stream containing trace quantities of acetylene compounds and elemental hydrogen into a selective hydrogenation zone to selectively hydrogenate at least a portion of said acetylene compounds and to produce an at least partially spent selective hydrogenation catalyst;

(b) passing the resulting effluent from said first selective hydrogenation zone in step (a) to a fractionation zone to produce a butadiene hydrocarbon stream having a reduced concentration of acetylene compounds;

(c) contacting the at least partially spent selective hydrogenation catalyst in said selective hydrogenation zone with a hexane solvent and hydrogen to reduce the polymer content of the selective hydrogenation catalyst to thereby increase hydrogenation activity;

(d) passing the resulting effluent from said selective hydrogenation zone to said fractionation zone to produce a stream comprising hexane solvent and polymer compounds;

(e) recycling at least a portion of said stream comprising hexane solvent and polymer compounds to provide at least a portion of said hexane solvent in step (c);

(f) recovering at least another portion of said stream comprising hexane solvent and polymer compounds;

(g) recovering said butadiene hydrocarbon stream having a reduced concentration of acetylene compounds produced in step (b); and (h) introducing said butadiene hydrocarbon stream containing trace quantities of acetylene compounds and elemental hydrogen into said selective hydrogenation zone after contact with said hexane solvent and hydrogen.

* * * * *